United States Patent [19]

Farrell et al.

[11] Patent Number: 4,687,741
[45] Date of Patent: Aug. 18, 1987

[54] NOVEL ENZYMES WHICH CATALYZE THE DEGRADATION AND MODIFICATION OF LIGNIN

[75] Inventors: Roberta L. Farrell, Danvers, Mass.; Thomas K. Kirk, Verona, Wis.; Ming Tien, State College, Pa.

[73] Assignee: Repligen Corporation, U.S. Sec. Agriculture, Cambridge, Mass.

[21] Appl. No.: 845,655

[22] Filed: Mar. 28, 1986

Related U.S. Application Data

[63] Continuation-in-part of Ser. No. 755,242, Jul. 15, 1985, abandoned.

[51] Int. Cl.$^4$ .................. C12N 9/02; C12N 15/00; C12N 1/14; C12N 9/14; D21C 3/00; C12R 1/645
[52] U.S. Cl. .................. 435/189; 435/254; 435/172.1; 435/911; 435/278; 162/72; 435/195
[58] Field of Search .............. 435/189, 195, 196, 278, 435/172.1, 254, 911

[56] References Cited

U.S. PATENT DOCUMENTS 3,962,033  6/1976  Eriksson et al. ............... 435/277
4,554,075  11/1985  Chang et al. .................. 210/611

OTHER PUBLICATIONS

Kirk et al., Enzyme Microb. Technology, 1981 vol. 3, pp. 189-196.
Tien et al., Proc. Natl. Acad. Sci. vol. 81, pp. 2280-2284, Apr. 1984.
Fems Microbiology Letters 28 (1985) pp. 119-123.
American Type Culture Collection (ATCC) Catalog of Strains 15$^{th}$ Edition, 1982 p. 441.
Higuchi, T. (1982) "Biodegration of Lignin: Biochemistry and Potential Applications" Experentia 38:159-166.
Janshekar, H. and Fiechter, A. (1983) "Advances in Biochemical Engineering/Biotechnology", A. Fiechter and T. W. Jeffries, EDs., vol. 27, pp. 119-178, Springer, Berlin.
Kirk, T. K. (1984) "Degradation of Lignin" in *Biochemistry of Microbial Degradation,* D. P. Gibson, Ed., pp. 399-437, Marcel Dekkar, N.Y.
Keyser, P., Kirk, T. K. and Zeikus, J. G. (1978) "Ligninolytic Enzyme System of *Phanerochaete chrysosporium*: Synthesized in the Absence of Lignin in Response to Nitrogen Starvation" J. Bacteriol. 135:790-797.
Leisola, M. et al., (1985) "Production, Purification and Some Reactions of Ligninases" Abstracts Lignin Biodegration Workshop, Vancouver, B.C., p. 10.
Gold, M. H. et al. (1985) "Spectral Characterization of the Extracellular Lignin Peroxidase of *Phanerochaete chrysosporium*" Abstracts Lignin Biodegradation Workshop, Vancouver, B.C. pp. 13-14.

*Primary Examiner*—Lionel M. Shapiro
*Attorney, Agent, or Firm*—Roman Saliwanchik; David R. Saliwanchik

[57] ABSTRACT

Novel lignin-degrading enzymes designated rLDM TM 1, rLDM TM 2, rLDM TM 3, rLDM TM 4, rLDM TM 5, and rLDM TM 6 are isolated and purified to the essentially pure form, wherein each rLDM TM is substantially free of other rLDM TM and native proteins, from the extracellular medium of a novel mutant microbe. The novel mutant, designated SC26, produces large amounts of the rLDM TM, thus facilitating the isolation and purification of them. These rLDM TM are useful in pulping processes to degrade and/or modify lignin.

8 Claims, No Drawings

NOVEL ENZYMES WHICH CATALYZE THE DEGRADATION AND MODIFICATION OF LIGNIN

CROSS REFERENCE TO A RELATED APPLICATION

This is a continuation-in-part of my copending application Ser. No. 775,242, filed on July 15, 1985, now abandoned.

BACKGROUND OF THE INVENTION

The invention disclosed herein is useful in several processes used by the pulp and paper industry. During pulping processes, cellulosic fibers must be liberated from their encasing lignin matrix so that they can associate with one another, yielding strength in the final product. This polymer separation can be accomplished by removal of lignin as in chemical pulps, or by maintaining the lignin as in high yield mechanical pulps. During the bleaching process, lignin is removed and the resulting pulp is brightened.

The secondary cell wall of wood, composed of cellulose fibrils, hemicellulose and lignin, imparts physical strength and rigidity to woody plants. The cellulose fibrils are densely packed and surround the cell in regular parallel arrays, or in crisscross layers. These fibrils are held together by a matrix of hemicellulose and lignin.

Cellulose is the most abundant component of woody tissue, comprising 35–45% of the dry weight. Cellulose is an ordered linear polymer of glucose monomers coupled by $\beta$-1,4 bonds. The hemicelluloses are branched polymers composed of pentose (5-carbon) monomers, normally xylose and arabinose; and hexose (6-carbon) monomers, consisting of glucose, galactose, mannose and substituted uronic acid.

Lignin is an extremely complex polymer formed by the free radical polymerization of substituted cinnamyl alcohol procursors. Lignin constitutes 15–35% of dry wood weight.

Lignin is highly resistant to biological attack; not a surprising finding considering the complexity and stability of lignin structure. No organism has been demonstrated to grow on lignin as the sole carbon source. The complex lignin polymer, however, is completely degraded by pure cultures of various higher order fungi. For reviews see Higuchi (1982) Experientia 38: 159–166, and Janshekar, H. and Feichter, A. (1983) "Advances in Biochemical Engineering/Biotechnology," A. Fiechter and T. W. Jeffries, Eds., Vol. 27, pp. 119–178, Springer, Berlin; Kirk, T. K. (1984) in "Biochemistry of Microbial Degradation," D. P. Gibson, Ed., pp. 339–437, Marcel Dekker, N.Y. The major degraders of "fully lignified" tissues (lignin >20%) are the basidiomycetes that cause the white-rot type of wood decay. The most extensive physiological investigations of lignin biogradation by white-rot fungi have been conducted with a single member of the family Corticraceae, *Phanerochaete chrysosporium* Burds.

Although *P. chrysosporium* is capable of completely degrading lignin, purified lignin will not support its growth. Purified cellulose, however, is a growth nutrient for these fungi. Lignin degradation allows these fungi to expose the cellulose food source contained within the lignin matrix. Under defined laboratory conditions, fungal lignin degradation is not observed during the approximately first 3 days of culture. Subsequently, the culture becomes starved for carbon or nitrogen. Lignin degradation is first observed one or two days later and is maximal at 6 days. The induction of lignin degradation in response to carbon and nitrogen starvation indicates that fungal lignin metabolism is a secondary metabolic event (Keyser, P., Kirk, T. K. and Zeikus, J. G. [1978] *J. Bacteriol.* 135: 790–797.).

Fungal lignin degradation is commercially impractical for several reasons. The rate of lignin degradation is unacceptably slow since ligninolytic activity must be induced by starvation. Furthermore, fungi metabolize cellulose fibers are their primary food source, resulting in reduced pulp yield and an inferior pulp product.

With regard to the major C—C and C—O—C intersubunit linkages found in lignin, it is important to note that approximately 80% of intersubunit bonds involve linkages to the $C_\alpha$ or $C_\beta$ carbons.

Tien and Kirk have disclosed a ligninase preparation capable of oxidatively cleaving $C_\alpha$-$C_\beta$ bonds in lignin model compounds (Tien, M. and Kirk, T. K. [1984] Proc. Natl. Acad. Sci. 81: 2280–2284). This preparation displays on an SDS-polyacrylamide gel predominantly one protein with an apparent molecular weight of 42 kilodaltons and several minor bands. Thus the preparation is a mixture of proteins without any means suggested for isolating the dominant protein from the minor bands. Subsequent to the publication of this paper, several scientific papers were published disclosing an inability to isolate the major protein from the mixture. These articles are as follows: Huynh, V-B and Crawford, R. L. (1985) FEMS Microbiology Letters 28: 119–123; Leisola, M. et al. (1985) Lignin Biodegradation Workshop; and Gold, M. H. et al. (1985) Lignin Biodegradation Workshop.

These protein isolations have been done by either ion-exchange chromatography or size exclusion-ion exchange column chromatography. The fractions containing ligninase have been analyzed by isoelectric focusing or SDS-polyacrylamide gel electrophoresis, and have shown multiple proteins. The scientists who performed this work are at the forefront of the lignin enzyme field, as evidenced by their participation in the Lignin Biodegradation Workshop held in Vancouver, BC in 1985.

With this background of prior art failures, the inventors of the subject invention were faced with a seemingly insurmountable problem. The invention disclosed herein has successfully solved the problem by producing a substantially pure preparation, designated rLDM TM 6, which is free of other proteins contained in the Tien and Kirk mixture disclosed above.

Advantageously, the preparation of the subject invention, rLDM TM 6, possesses desirable properties for use in pulping wood and treating effluent which the Tien and Kirk preparation did not have. Specifically, the Tien and Kirk mixture has a lower specific activity than the rLDM TM 6 of the subject invention.

There is a clear need to isolate and identify other enzymes which can be used to catalyze the degradation and modification of lignin. The novel rLDM TM of the subject invention are useful for this purpose.

These novel compounds are lignin-degrading enzymes which will not attack cellulose or hemicellulose. The enzymes are immediately active and require no metabolic induction; therefore they overcome the drawbacks of fungi previously mentioned for use in pulp operations.

BRIEF SUMMARY OF THE INVENTION

The subject invention concerns novel lignin-degrading enzymes which are called rLDM TM 1, rLDM TM 2, rLDM TM 3, rLDM TM 4, rLDM TM 5, and rLDM TM 6. These novel compounds, advantageously, possess the properties of (1) reducing the amount of lignin in kraft pulp, (2) enhancing the strength properties of thermomechanical pulp (TMP) and (3) decolorizing kraft lignin. The rLDM TM of the subject invention are characterized herein by the critical property of being able to catalyze the oxidation of veratryl alcohol to veratrylaldehyde, and the following physical parameters:

(1) molecular weight as determined by SDS-PAGE;
(2) amino acid composition;
(3) heme content;
(4) homology by antibody reactivity;
(5) specificity of activity against lignin model substrates; and
(6) elution from a FPLC column at specified sodium acetate molarities.

The lignin-degrading enzymes of the invention, referred to as rLDM TM, are referred to as Pulpases TM in co-pending application Ser. No. 755,242.

DETAILED DESCRIPTION OF THE INVENTION

The isolation of the novel rLDM TM of the subject invention was facilitated by use of a novel stable mutant strain of *Phanerochaete chrysosporium*, which elaborates high amounts of ligninolytic enzymes into the fermentation medium. The novel mutant strain, designated SC26, has been deposited in the permanent collection of a public culture repository, to be maintained for at least 30 years. The culture repository is the Northern Regional Research Laboratory, U.S. Dept. of Argiculture, Peoria, Ill. 61604, USA. The accession number is NRRL 15978, and the deposit date is July 3, 1985. This deposited culture is available to the public upon the grant of a patent disclosing it. The deposit also is available as required by foreign patent laws in countries wherein counterparts of the subject application, or its progeny, are filed. However, it should be understood that the availability of a deposit does not constitute a license to practice the subject invention in derogation of patent rights granted by governmental action.

Novel mutant SC26 was obtained by UV mutagenesis of the wild type *Phanerocheate chrysosporium*, ATCC 24725.

Novel mutant SC26 was grown on a nitrogen-limited trace element medium supplemented with glucose and buffered at pH 4.5.

Ligninase activity in the fermentation medium was measured periodically by standard means determining the rate of oxidation of veratryl alcohol to veratrylaldehyde.

Isolation and purification of the novel rLDM TM of the subject invention from the extracellular fluid in the fermentation was accomplished by ultrafiltration and FPLC using an anion exchange column.

Following are examples which illustrate the novel enzymes and procedures, including the best mode, for practicing the invention. These examples should not be construed as limiting. All percentages are by weight and all solvent mixture proportions are by volume unless otherwise noted.

EXAMPLE 1

Growth of Mutant SC26 (NRRL 15978) to Product Fermentation Medium Containing Novel Ligninaes Inoculum was prepared by homogenizing 50 ml of 1.5-day cultures of mutant SC26 grown in 1 liter flasks containing the following medium, designated nitrogen-limited BIII/glucose medium:

The BIII medium contains $1.08 \times 10^{-3}$M ammonium tartrate, $1.47 \times 10^{-2}$M $KH_2PO_4$, $2.03 \times 10^{-3}$M $MgSO_4.7H_2O$, $6.8 \times 10^{-4}$M $CaCl_2.2H_2O$, $2.96 \times 10^{-6}$M thiamine.HCl an 10 ml.$L^{-1}$ of a trace element solution. The trace element solution contains $7.8 \times 10^{-3}$M nitriloacetic acid, $1.2 \times 10^{-2}$M $MgSO_4.7H_2O$, $1.7 \times 10^{-2}$M NaCl, $3.59 \times 10^{-4}$M $FeSO_4.7H_2O$, $7.75 \times 10^{-4}$M $CoCl_2$, $9.0 \times 10^{-4}$M $CaCl_2$, $3.48 \times 10^{-4}$M $ZnSO_4.7H_2O$, $4 \times 10^{-5}$M $CuSO_4.5H_2O$, $2.1 \times 10^{-5}$M $AlK(SO_4)_2.12H_2O$, $1.6 \times 10^{-4}$M $H_3BO_3$, $4.1 \times 10^{-5}$M $NaMoO_4.2H_2O$ and $2.9 \times 10^{-3}$M $MnSO_4.H_2O$.

The medium was supplemented with 10% (by wt/liter) of glucose.

The medium was buffered with 10 mM trans-aconitic acid, pH 4.5.

Flasks (125 ml, containing 10 ml sterile medium having the above-described medium) were each inoculated with 0.5 ml of the above homogenate and kept stationary at 39° C. The flasks were flushed on days 0, 3, and 6 with water-saturated $O_2$. Alternatively, a rotating biological contractor (RBC) was used to grow the fungus. 2.5 liters of the above-described medium was inoculated with 100 ml of the above homogenate and grown at 39° C. with the RBC rotating at 1 rpm with continuous oxygenation.

Logninase activity was measured periodically by determining the rate of oxidation of veratryl alcohol to veratrylaldehyde. Reaction mixtures contained 275 μl of extracellular fluid (from flasks or the RBC), 2 mM veratryl alcohol, 0.4 mM $H_2O_2$ and 0.1 mM sodium tartrate, pH 2.5 in a final volume of 0.5 ml. The reactions were started by $H_2O_2$ addition immediately after buffer was added and were monitored at 310 nm. Protein was determined according to Bradford (Bradford, M. M. [1976] Anal. Biochem. 72: 248–254) using bovine serum albumin (Sigma Chemical, St. Louis, MO) as standard.

EXAMPLE 2

Isolation and Purification of the Novel rLDM TM

The extracellular growth media from cultures grown in flasks, as described above, was harvested by centrifugation at 5000×G, 10 min, 4° C. Extracellular growth media was then concentrated by ultrafiltration through a 10K filter. The resulting concentrate is called the Ligninolytic Mixture TM. The rLDM TM contained in this Ligninolytic Mixture TM were separated by fast protein liquid chromatography (FPLC) using a Pharmacia Mono Q column (Pharmacia, Piscataway, NJ) and a gradient of sodium acetate buffer, pH 6, from 10 mM to 1M. rLDM TM 1, 2, 3, 4, 5, and 6 elute from the column in a typical preparation at the following sodium acetate molarities, respectively: 0.16, 0.18, 0.34, 0.40, 0.58, and 0.43M to give essentially opure rLDM TM 1-6. Each rLDM TM is substantially free of other rLDM TM and native proteins.

Characterization of the Novel rLDM TM

The rLDM TM have been characterized by the following criteria:
1. ability to catalyze the oxidation of veratryl alcohol to veratrylaldehyde;
2. molecular weight as determined by SDS-PAGE;
3. amino acid composition;
4. heme content;
5. homology by antibody reactivity;
6. specificity of activity against lignin model substrates; and
7. elution from an FPLC column at specified sodium acetate molarities.

All of the rLDM TM catalyze the oxidation of veratryl alcohol to veratryladehyde, as monitored spectrophotometrically at 310 nm. A unit of activity is defined as the production of 1 micromole of veratrylaldehyde in the rLDM TM catalyzed reactions. The specific activities of typical preparations at about 24° C. are as follows:

| rLDM TM | 1 | 2 | 3 | 4 | 5 | 6 |
|---|---|---|---|---|---|---|
| SPECIFIC ACTIVITY UNITS/MG · MINUTE | 2.6 | 17.1 | 5.1 | 9.7 | 9.4 | 12.4 |
| MOLECULAR WEIGHT kD | 38 | 38 | 42 | 42 | 43 | 42 |

Amino acid composition—See Table 1.

Heme and carbohydrate content—rLDM TM 1, 2, 3, 4, 5, and 6 each contain a single protoheme IX moiety. All are glycosylated according to periodic acid staining (PAS) and binding to Con A-Sepharose (Sigma).

TABLE I

Amino Acid Composition of rLDM TM

| Amino Acid | rLDM TM 1 Ratio | rLDM TM 2 Ratio | rLDM TM 3 Ratio | rLDM TM 5 Ratio | rLDM TM 6 Ratio |
|---|---|---|---|---|---|
| asp/asn | 1.4 | 2.0 | 5.4 | 5.0 | 3.0 |
| glu/gln | 6.0 | 7.7 | 16.8 | 19.9 | 8.0 |
| ser | 4.3 | 4.1 | 14.0 | 22.3 | 6.8 |
| his | 4.4 | 3.2 | 7.3 | 15.9 | 3.2 |
| gly | 6.5 | 5.7 | 24.0 | 44.7 | 8.3 |
| thr | 2.2 | 3.5 | — | — | 4.9 |
| arg | 1.1 | 1.2 | 2.9 | 4.8 | 1.3 |
| ala | 7.3 | 7.9 | 14.4 | 13.8 | 6.7 |
| tyr | 0.2 | — | 1.0 | 1.0 | 0.2 |
| met | — | — | 1.2 | — | 0.14 |
| val | 1.6 | 2.6 | 7.4 | 6.5 | 4.2 |
| phe | 1.1 | 3.0 | 7.0 | 3.3 | 3.2 |
| ile | 1.0 | 2.2 | 4.1 | 3.6 | 2.4 |
| leu | 1.5 | 2.6 | 6.5 | 6.0 | 3.3 |
| lys | 0.5 | 1.0 | 2.5 | 2.3 | 1.0 |

Immunoblot Procedure

This procedure was used to further characterize the rLDM TM. It is a standard procedure which is disclosed in Towbin et al. (Towbin, H., Staehelin, T. and Gordon, J. [1979] Proc. Natl. Acad. Sci. USA 76: 4350). The procedure involves separating the proteins by electrophoresis in a gel, transfer of the proteins to a solid matrix, and reacting with (1) a primary probe, rabbit anti-rLDM TM antibody and (2) a secondary probe, goat anti-rabbit antibody coupled to horseradish peroxidase.

rLDM TM 1, 3, 4, 5, and 6 react to polyclonal antibodies made to rLDM TM 2 and 6, using the above immunoblot procedures. rLDM TM 2, in the same procedure, reacts to polyclonal antibodies made to rLDM TM 6.

All the rLDM TM disclosed herein have the following unique activities on lignin model substrates:
1. oxidative cleavage of $C_\alpha$–$C_{62}$;
2. hydroxylation of benzylic methylene groups;
3. oxidation of benzyl alcohols to aldehydes;
4. phenol oxidation; and
5. oxidative cleavage of methoxyl groups.

"Lignin model substrates" are chemicals which resemble parts of lignin. The above activities are characteristic of the rLDM TM disclosed herein.

EXAMPLE 3

Bleaching of Kraft Pulp with rLDM TM rLDM TM 1–6, alone, or mixtures thereof, are added to kraft pulp having a characteristic brown color at 3% consistency in 10 mM trans-aconitic acid, pH 4.5, 400 $\mu$M $H_2O_2$ and 100 $\mu$M $MnSO_4$. The pulp slurry is flushed with $O_2$ and incubated with slow shaking at 39° C. for 12 hr, after which the kraft pulp solution is decanted, and a 1M NaOH solution is added to the pulp and incubated for 60 min at 65° C. This is then decanted and the kraft pulp is washed in water. The resulting kraft pulp no longer has a dark brown color, but instead has a desired lighter color.

The use of $MnSO_4$ is optional.

EXAMPLE 4

Treatment of Thermomechanical Pulp (TMP) with rLDM TM rLDM TM 1–6, alone, or mixtures thereof, are added to 10 gm of TMP (dry weight) at 3% consistency in 10 mM trans-aconitic acid, pH 4.5, 400 $\mu$M $H_2O_2$ and 100 $\mu$M $MnSO_4$. The pulp slurry is flushed with $O_2$ and incubated with slow shaking at 39° C. for 12 hr, after which time the TMP is washed with water. The tensile, tear and burst indices as well as breaking length of the pulp are measured and found to be of enhanced strength versus an untreated sample. The brightness reversion of the treated sample is less than the untreated sample; therefore, brightness stability is increased with the rLDM TM treatment.

The use of $MnSO_4$ is optional.

The rLDM TM of the subject invention can be used in the crude form, in a purified form, wherein each rLDM TM is substantially free of other rLDM TM and native proteins, and in mixtures thereof. It is well within the skill of a person skilled in the art to adjust amounts of rLDM ™ used in accordance with the purity of the rLDM ™ preparation.

"Native proteins" as used herein refers to other proteins present in the extracellular fermentation medium, as described above.

EXAMPLE 5

Treatment of Wood Pulp with rLDM ™

One part of wood pulp is treated with about $10 \times 10^{-6}$ to about $20 \times 10^{-6}$ parts of a rLDM ™ in about 40 mM trans-aconitic acid, pH 4.5, at about 39° C. for about 1 to about 16 hr. The pulp is then washed in about 1M NaOH at about 65° C. for about 1 hr, and rinsed in water. This treatment of the wood pulp results in the removal of about ⅓ of the lignin as evidenced by the reduction of kappa number from about 18 to about 13.

We claim:

1. rLDM ™ 1, substantially free of other rLDM ™ and deleterious native proteins, having the following characteristics:
   (a) catalyzes the oxidation of veratryl alcohol to veratrylaldehyde at about 2.6 units/mg.min.;
   (b) has a molecular weight of about 38 kilodaltons;
   (c) contains a single protoheme IX moiety;
   (d) is glycosylated;
   (e) contains the following amino acid ratio:

| Amino Acid | rLDM ™ 1 Ratio |
|---|---|
| asp/asn | 1.4 |
| glu/gln | 6.0 |
| ser | 4.3 |
| his | 4.4 |
| gly | 6.5 |
| thr | 2.2 |
| arg | 1.1 |
| ala | 7.3 |
| tyr | 0.2 |
| met | — |
| val | 1.6 |
| phe | 1.1 |
| ile | 1.0 |
| leu | 1.5 |
| lys | 0.5; |

(f) reacts to polyclonal antibodies made to rLDM ™ 2 and 6 in an immunoblot procedure;
   (g) elutes from an FPLC column at a sodium acetate molarity of about 0.16; and
   (h) has the following activities on lignin model substrates:
      (1) oxidative cleavage of $C_\alpha$-$C_\beta$;
      (2) hydroxylation of benzylic methylene groups;
      (3) oxidation of benzyl alcohols to aldehydes;
      (4) phenol oxidation; and
      (5) oxidative cleavage of methoxyl groups.

2. rLDM ™ 2, substantially free of other rLDM ™ and deleterious native proteins, having the following characteristics:
   (a) catalyzes the oxidation of veratryl alcohol to veratrylaldehyde at about 17.1 units/mg.min;
   (b) has a molecular weight of about 38 kilodaltons;
   (c) contains a single protoheme IX moiety;
   (d) is glycosylated;
   (e) contains the following amino acid ratio:

| Amino Acid | r LDM ™ 2 Ratio |
|---|---|
| asp/asn | 2.0 |
| glu/gln | 7.7 |
| ser | 4.1 |
| his | 3.2 |
| gly | 5.7 |
| thr | 3.5 |
| arg | 1.2 |
| ala | 7.9 |
| tyr | — |
| met | — |
| val | 2.6 |
| phe | 3.0 |
| ile | 2.2 |
| leu | 6.5 |
| lys | 2.5 |

(f) reacts to a polyclonal antibody made to rLDM ™ 6 in an immunoblot procedure;
   (g) elutes from an FPLC column at a sodium acetate molarity of about 0.18; and
   (h) has the following activities on lignin model substrates:
      (1) oxidative cleavage of $C_\alpha$-$C_{62}$;
      (2) hydroxylation of benzylic methylene groups;
      (3) oxidation of benzyl alcohols to aldehydes;
      (4) phenol oxidation; and
      (5) oxidative cleavage of methoxyl groups.

3. rLDM ™ 3, substantially free of other rLDM ™ and deleterious native proteins, having the following characteristics:
   (a) catalyzes the oxidation of veratryl alcohol to veratrylaldehyde at about 5.1 units/mg.min;
   (b) has a molecular weight of about 42 kilodaltons;
   (c) contains a single protoheme IX moiety;
   (d) is glycosylated;
   (e) contains the following amino acid ratio:

| Amino Acid | rLDM ™ 3 Ratio |
|---|---|
| asp/asn | 5.4 |
| glu/gln | 16.8 |
| ser | 14.0 |
| his | 7.3 |
| gly | 24.0 |
| thr | — |
| arg | 2.9 |
| ala | 14.4 |
| tyr | 1.0 |
| met | 1.2 |
| val | 7.4 |
| phe | 7.0 |
| ile | 4.1 |
| leu | 6.5 |
| lys | 2.5 |

(f) reacts to polyclonal antibodies made to rLDM ™ 2 and 6 in an immunoblot procedure;
   (g) elutes from an FPLC column at a sodium acetate molarity of about 0.34; and
   (h) has the following activities on lignin model substrates:
      (1) oxidative cleavage of $C_\alpha$-$C_\beta$;
      (2) hydroxylation of benzylic methylene groups;
      (3) oxidation of benzyl alcohols to aldehydes;
      (4) phenol oxidation; and
      (5) oxidative cleavage of methoxyl groups.

4. rLDM ™ 4, substantially free of other rLDM ™ and deleterious native proteins, having the following characteristics:
   (a) catalyzes the oxidation of veratryl alcohol to veratrylaldehyde at about 9.7 units/mg.min;
   (b) has a molecular weight of about 42 kilodaltons;
   (c) contains a single protoheme IX moiety;
   (d) is glycosylated;
   (e) reacts to polyclonal antibodies made to rLDM ™ 2 and 6 in an immunoblot procedure;
   (f) elutes from an FPLC column at a sodium acetate molarity of about 0.40; and
   (g) has the following activities on lignin model substrates:
      (1) oxidative cleavage of $C_\alpha$–$C_\beta$;
      (2) hydroxylation of benzylic methylene groups;
      (3) oxidation of benzyl alcohols to aldehydes;
      (4) phenol oxidation; and
      (5) oxidative cleavage of methoxyl groups.

5. rLDM ™ 5, substantially free of other rLDM ™ and deleterious native proteins, having the following characteristics:
   (a) catalyzes the oxidation of veratryl alcohol to veratrylaldehyde at about 9.4 units/mg.min.;
   (b) has a molecular weight of about 4.3 kilodaltons;
   (c) contains a single protoheme IX moiety;
   (d) is glycosylated;
   (e) contains the following amino acid ratio:

| Amino Acid | rLDM ™ 5 Ratio |
| --- | --- |
| asp/asn | 5.0 |
| glu/gln | 19.9 |
| ser | 22.3 |
| his | 15.9 |
| gly | 44.7 |
| thr | — |
| arg | 4.8 |
| ala | 13.8 |
| tyr | 1.0 |
| met | — |
| val | 6.5 |
| phe | 3.3 |
| ile | 3.6 |
| leu | 6.0 |
| lys | 2.3 |

(f) reacts to polyclonal antibodies made to rLDM ™ 2 and 6 in an immunoblot procedure;
   (g) elutes from an FPLC column at a sodium acetate molarity of about 0.58; and
   (h) has the following activities on lignin model substrates:
      (1) oxidative cleavage of $C_\alpha$–$C_\beta$;
      (2) hydroxylation of benzylic methylene groups;
      (3) oxidation of benzyl alcohols to aldehydes;
      (4) phenol oxidation; and
      (5) oxidative cleavage of methoxyl groups.

6. rLDM ™ 6, substantially free of other rLDM ™ and deleterious native proteins, having the following characteristics:
   (a) catalyzes the oxidation of veratryl alcohol to veratrylaldehyde at about 12.4 units/mg.min.;
   (b) has a molecular weight of about 42 kilodaltons;
   (c) contains a single protoheme IX moiety;
   (d) is glycosylated;
   (e) contains the following amino acid ratio:

| Amino Acid | rLDM ™ 6 Ratio |
| --- | --- |
| asp/asn | 3.0 |
| glu/gln | 8.0 |
| ser | 6.8 |
| his | 3.2 |
| gly | 8.3 |
| thr | 4.9 |
| arg | 1.3 |
| ala | 6.7 |
| tyr | 0.2 |
| met | 0.14 |
| val | 4.2 |
| phe | 3.2 |
| ile | 2.4 |
| leu | 3.3 |
| lys | 1.0 |

(f) reacts to polyclonal antibodies made to rLDM ™ 2 and 6 in an immunoblot procedure;
   (g) elutes from an FPLC column at a sodium acetate molarity of about 0.43; and
   (h) has the following activities on lignin model substrates:
      (1) oxidative cleavage of $C_\alpha$–$C_\beta$;
      (2) hydroxylation of benzylic methylene groups;
      (3) oxidation of benzyl alcohols to aldehydes;
      (4) phenol oxidation; and
      (5) oxidative cleavage of methoxyl groups.

7. A process for degrading and modifying lignin which comprises treating wood pulp with a compound selected from the group consisting of rLDM ™ 1, rLDM ™ 2, rLDM ™ 3, rLDM ™ 4, rLDM ™ 5, and rLDM ™ 6.

8. A biologically pure mutuant culture of *Phanerochaete chrysosporium*, designated mutant SC26, and having the culture deposit number NRRL 15978, which mutuant, upon being grown in a suitable medium, elaborates rLDM ™ 1, rLDM ™ 2, rLDM ™ 3, rLDM ™ 4, rLDM ™ 5, and rLDM ™ 6 into the medium.

* * * * *

UNITED STATES PATENT AND TRADEMARK OFFICE
CERTIFICATE OF CORRECTION

PATENT NO. : 4,687,741
DATED : August 18, 1987
INVENTOR(S) : Roberta L. Farrell, Thomas K. Kirk, Ming Tien It is certified that error appears in the above-identified patent and that said Letters Patent are hereby corrected as shown below:

| | | |
|---|---|---|
| Col. 2: | line 12: | "are" should read --as--. |
| Col. 4: | line 12: | "an" should read --and--; line 37: "Logninase" should read --Ligninase--; line 55: "5000XG" should read --5000 xG--. |
| Col. 6: | line 5: | "$C_\alpha - C_{62}$" should read --$C_\alpha - C_\beta$--. |
| Claim 2: | line 25: | "$C_\alpha - C_{62}$" should read --$C_\alpha - C_\beta$--. |
| Claim 5: | line 6: | "4.3" should read --43--. |

Signed and Sealed this

Fifth Day of April, 1988

*Attest:*

DONALD J. QUIGG

*Attesting Officer*  *Commissioner of Patents and Trademarks*